United States Patent [19]

Kirkpatrick et al.

[11] 4,226,873
[45] Oct. 7, 1980

[54] 5-SUBSTITUTED-3-FLUOROSULFONYL-4H-1,2,4-TRIAZOLES AND USE AS INSECTICIDES AND MITICIDES

[75] Inventors: Joel L. Kirkpatrick, Overland Park; William C. Doyle, Jr., Leawood, both of Kans.

[73] Assignee: Gulf Oil Corporation, Pittsburgh, Pa.

[21] Appl. No.: 771,133

[22] Filed: Feb. 23, 1977

Related U.S. Application Data

[63] Continuation-in-part of Ser. No. 697,505, Jun. 18, 1976, abandoned.

[51] Int. Cl.³ .................. A01N 43/64; C07D 249/12
[52] U.S. Cl. ..................................... 424/269; 548/265
[58] Field of Search ............... 260/308 R; 424/269; 548/265

[56] References Cited

U.S. PATENT DOCUMENTS

| | | | |
|---|---|---|---|
| 2,554,816 | 5/1951 | Clapp et al. | 260/308 D |
| 2,744,907 | 5/1956 | Young et al. | 260/308 R |
| 3,966,754 | 6/1976 | Böhner et al. | 260/308 R |

OTHER PUBLICATIONS

Blackman et al., I, J. Chem. Soc., (London), 1967, pp. 661–662.
Blackman et al. II, J. Chem. Soc., C, (London), 1970, pp. 2403–2409.

*Primary Examiner*—Alton D. Rollins
*Attorney, Agent, or Firm*—Carl A. Cline

[57] ABSTRACT

New fluorosulfonyltriazole compounds which are useful as miticides and insecticides have the general structural formula

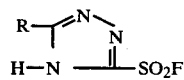

and tautomeric forms thereof, in which R is hydrogen, $C_1$ to $C_7$ alkyl, alkoxyalkyl, phenoxyalkyl, benzyl, phenyl or $C_3$ to $C_6$ cycloalkyl.

38 Claims, No Drawings

5-SUBSTITUTED-3-FLUOROSULFONYL-4H-1,2,4-TRIAZOLES AND USE AS INSECTICIDES AND MITICIDES

This application is a continuation-in-part of U.S. patent application Ser. No. 697,505, filed June 18, 1976, now abandoned.

DESCRIPTION OF THE INVENTION

We have discovered a new class of compounds which are useful as miticides and insecticides which may be represented by the general structural formula

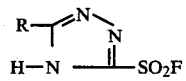

in which R is hydrogen, $C_1$ to $C_7$ alkyl, branched or unbranched, which may also have lower alkoxy ($C_1$ to $C_4$) or phenoxy substituents, benzyl, phenyl or $C_3$ to $C_6$ cycloalkyl. It will be understood that with triazoles of this type in which a free proton is attached to a nitrogen atom, tautomerism may occur, as the proton may migrate from one nitrogen to another, with a consequent shift in the double bonds in the molecule. The tautomeric forms of the novel compounds are therefore included within the scope of the invention disclosed and claimed herein.

A. SYNTHESIS OF THE COMPOUNDS

The new compounds may be prepared by means of a succession of procedures, as outlined below:

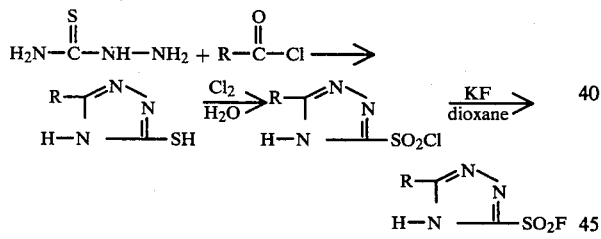

Below are detailed descriptions of illustrative procedures.

PREPARATION OF 3-TERT.BUTYL-4H-1,2,4-TRIAZOLIN-5-THIONE

To a suspension of 50 g (0.55 mol) of thiosemicarbazide and 43 g (0.05 mol) of pyridine in 300 ml of dioxane was added 42.6 g (0.6 mol) of pivalyl chloride, with cooling. The reaction was stirred at room temperature for 72 hours, then poured into water. The resulting solid was collected, washed with water and dried. The unpurified pivalyl thiosemicarbazide was heated at reflux temperature in 300 ml of 10% sodium hydroxide solution for 3 hours. After cooling, the pH was adjusted to 4 with hydrochloric acid and the product collected, washed with water and dried to give 43.8 g, m.p. 200°–203°. Recrystallization from methanol-chloroform gave a sample m.p. 203°–205°.

Additional compounds prepared by this method, or that described in Org. Syn., 40, 99 (1960), are listed in Table A.

TABLE A

Compounds of the Formula

| R | MP, °C. |
|---|---|
| H | 230–233 (dec) |
| methyl | 275–277 (dec) |
| ethyl | 262–265 |
| propyl | 224–226 |
| isopropyl | 186–187 |
| cyclopropyl | 262–263 |
| butyl | 199–201 |
| 2-methylpropyl | 180–182 |
| benzyl | 216–221 |
| pentyl | 190–193 |
| 1-ethylpropyl | 194–195 |
| methoxymethyl | 189–190 |
| 1-phenoxyethyl | 93–95 |

PREPARATION OF 3-FLUOROSULFONYL-5-TERT.BUTYL-4H-1,2,4-TRIAZOLE

To a slurry of 20 g of 3-tert.butyl-4H-1,2,4-triazolin-5-thione in 200 ml of 10% NaCl was added chlorine gas through a delivery tube below the surface. The temperature was maintained at 0 to −5¼ by means of an ice-salt bath. When the absorption of the chlorine was complete, as evidenced by an equilibrium of flow rates into and from the reaction, the slurry was filtered, the solid washed with water and partially dried. The damp 3-chlorosulfonyl-5-tert.butyl-4H-1,2,4-triazole was then dissolved in a mixture of 55 ml dioxane and 5.5 ml dimethyl formamide and an aqueous solution of KF (16.2 g KF in 14 ml water) was added. The reaction was heated at reflux temperature with stirring for 2 hrs, then taken to near dryness. Upon the addition of water, the crude 3-fluorosulfonyl-5-tert.butyl-4H-1,2,4-triazole precipitated and was collected. Recrystallization from $CHCl_3$—petroleum ether gave 8.7 g of the product, mp 175–177¼.

This compound and others made by the same general procedure are listed in Table B.

TABLE B

Compounds of the Formula

| COMPOUND NO. | R | MP °C. |
|---|---|---|
| 1 | H | 82–85 (dec) |
| 2 | methyl | 129–130 |
| 3 | ethyl | 115–118 |
| 4 | propyl | 108–109 |
| 5 | isopropyl | 154–155 |
| 6 | cyclopropyl | 159–162 |
| 7 | butyl | 90–91 |
| 8 | tert. butyl | 175–177 |
| 9 | benzyl | 139–141 |
| 10 | 2-methylpropyl | 105–106 |
| 11 | pentyl | 95–97 |
| 12 | 1-ethylpropyl | 122–124 |
| 13 | methoxymethyl | 48–51 |
| 14 | 1-phenoxyethyl | 175–178 |
| 15 | phenyl | 144–147 |

TABLE B-continued

Compounds of the Formula

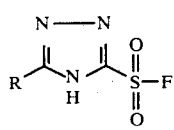

| COMPOUND NO. | R | MP °C. |
|---|---|---|
| 16 | 1-heptyl | 82–84 |
| 17 | 3-methylbutyl (isoamyl) | 93–94 |
| 18 | 2,2-dimethylpropyl | 102–104 |
| 19 | 2-pentyl | oil |
| 20 | 3-heptyl | oil |
| 21 | cyclohexyl | wax |

B. COMBATING INSECTS AND MITES

The combating of insects and mites may be demonstrated by the procedure described below.

Each chemical compound is formulated at 500 ppm concentration by dissolving 25 mg of the compound in 5 ml of acetone, adding to the resulting solution in a 50 ml. volumetric flask sufficient 0.12 percent aqueous solution of octylphenoxy polyoxyethanol surfactant to bring the volume up to the mark and mixing by shaking. Lower concentrations are obtained by dilution with water.

METHOD FOR MITES, APHIDS, BEAN BEETLES AND ARMY WORMS

Three 5 oz paper cups containing Henderson dwarf lima bean plants and one 5 oz paper cup containing Orange Gem Nasturtiums, all growing in vermiculite, are placed on a turntable and sprayed to thorough wetness with 25 ml of a solution of the candidate chemical at the appropriate concentration. Nasturtiums were already infested with 50-100 bean aphids (BA). A bean plant in one paper cup was already infested with 50-100 two-spotted mites (TSM). Leaves from the two remaining bean plants are removed following spraying and placed in disposable petri dishes with 5 southern armyworm (SA) larvae in one petri dish, and 5 Mexican bean beetle (MBB) larvae in the other petri dish. The rating is done approximately 48 hours after spraying as follows:

| RESULT | RATING |
|---|---|
| None dead | 0 |
| 1–25% dead | 1 |
| 26–50% dead | 2 |
| 51–75% dead | 3 |
| 76–99%+ dead | 4 |
| 100% dead | 5 |

Results of tests performed on a group of the compounds at concentrations of up to 500 ppm appear in the following table:

TABLE C

| Compound No. | Conc. PPM | MBB | SA | BA | TSM |
|---|---|---|---|---|---|
| 1 | 500 | 0 | 0 | 0 | 5 |
|  | 250 |  |  |  | 5 |
|  | 125 |  |  |  | 5 |
|  | 62 |  |  |  | 5 |
|  | 31 |  |  |  | 4 |
|  | 15 |  |  |  | 0 |
| 2 | 500 | 3 | 5 | 0 | 4 |
|  | 250 | 4 | 0 | 3 | 4 |
|  | 125 | 4 | 0 | 3 | 4 |
|  | 62 | 3 | 0 | 2 | 4 |
|  | 31 | 1 | 0 | 1 | 4 |
|  | 15 | 2 | 0 | 1 | 4 |
| 3 | 500 | 5 | 5 | 4 | 5 |
|  | 250 | 5 | 1 | 5 | 5 |
|  | 125 | 5 | 2 | 5 | 5 |
|  | 62 | 5 | 0 | 2 | 5 |
|  | 31 | 5 | 0 | 0 | 5 |
|  | 15 | 5 | 0 | 0 | 5 |
| 4 | 500 | 5 | 3 | 4 | 5 |
|  | 250 | 4 | 0 | 4 | 5 |
|  | 125 | 5 | 0 | 1 | 5 |
|  | 62 | 5 | 0 | 0 | 5 |
|  | 31 | 5 | 0 | 0 | 5 |
|  | 15 | 5 | 0 | 0 | 5 |
| 5 | 500 | 5 | 5 | 5 | 5 |
|  | 250 | 4 | 0 | 5 | 5 |
|  | 125 | 5 | 0 | 4 | 5 |
|  | 62 | 5 | 0 | 1 | 5 |
|  | 31 | 5 | 0 | 0 | 5 |
|  | 15 | 5 | 0 | 0 | 5 |
| 6 | 500 | 5 | 5 | 4 | 5 |
|  | 250 | 5 | 3 | 3 | 5 |
|  | 125 | 5 | 3 | 1 | 5 |
|  | 62 | 5 | 0 | 0 | 5 |
|  | 31 | 5 | 0 | 0 | 5 |
|  | 15 | 5 | 0 | 0 | 5 |
| 7 | 500 | 5 | 0 | 0 | 5 |
|  | 250 | 3 |  |  | 5 |
|  | 125 | 3 |  |  | 5 |
|  | 62 | 0 |  |  | 4 |
|  | 31 | 0 |  |  | 4 |
|  | 15 | 0 |  |  | 4 |
| 8 | 500 | 5 | 5 | 5 | 5 |
|  | 250 | 5 | 0 | 4 | 5 |
|  | 125 | 5 | 0 | 4 | 5 |
|  | 62 | 5 | 0 | 3 | 5 |
|  | 31 | 5 | 0 | 3 | 5 |
|  | 15 | 5 | 0 | 1 | 5 |
| 9 | 500 | 2 | 0 | 0 | 4 |
|  | 250 | 0 |  |  | 4 |
|  | 125 | 0 |  |  | 4 |
|  | 62 | 0 |  |  | 3 |
|  | 31 | 0 |  |  | 3 |
|  | 15 | 0 |  |  | 1 |
| 10 | 500 | 4 | 1 | 3 | 5 |
|  | 250 | 5 |  | 0 | 4 |
|  | 125 | 1 |  | 0 | 5 |
|  | 62 | 0 |  | 0 | 5 |
|  | 31 | 0 |  | 0 | 4 |
|  | 15 | 0 |  | 0 | 2 |
| 11 | 500 | 5 | 0 | 0 | 4 |
|  | 250 | 5 |  |  | 5 |
|  | 125 | 2 |  |  | 4 |
|  | 62 | 0 |  |  | 4 |
|  | 31 | 0 |  |  | 4 |
|  | 15 | 0 |  |  | 0 |
| 12 | 500 | 4 | 0 | 0 | 5 |
| 13 | 500 | 5 | 0 | 3 | 5 |
|  | 250 | 5 | 0 | 2 | 4 |
|  | 125 | — | 0 | 1 | 4 |
|  | 62 | 3 | 0 | 0 | 4 |
|  | 31 | 0 | 0 | 0 | 3 |
|  | 15 | 0 | 0 | 0 | 3 |
| 14 | 500 | 5 | 0 | 2 | 4 |
|  | 250 | 5 | 0 | 0 | 5 |
|  | 125 | — | 0 | 0 | 4 |
|  | 62 | 0 | 0 | 0 | 2 |
|  | 31 | — | 0 | 0 | 1 |
|  | 15 | 1 | 0 | 0 | 0 |
| 15 | 500 | 0 | 0 | 0 | 3 |
|  | 250 |  |  |  | 0 |
|  | 125 |  |  |  | 0 |

TABLE C-continued

Results of Insecticide and Miticide Tests

| Compound No. | Conc. PPM | MBB | SA | BA | TSM |
|---|---|---|---|---|---|
|  | 62 |  |  |  | 0 |
|  | 31 |  |  |  | 0 |
|  | 15 |  |  |  | 0 |
| 16 | 500 | 5 | 0 | 0 | 2 |
|  | 250 | 3 |  |  | 4 |
|  | 125 | 2 |  |  | 0 |
|  | 62 | 1 |  |  | 0 |
|  | 31 | 0 |  |  | 2 |
|  | 15 | 0 |  |  | 0 |
| 17 | 500 | 0 | 0 | 2 | 4 |
|  | 250 |  |  |  | 4 |
|  | 125 |  |  |  | 3 |
|  | 62 |  |  |  | 2 |
|  | 31 |  |  |  | 1 |
|  | 15 |  |  |  | 0 |
| 18 | 500 | 5 | 0 | 4 | 4 |
|  | 250 | 5 |  | 0 | 2 |
|  | 125 | 5 |  | 0 | 2 |
|  | 62 | 5 |  | 0 | 0 |
|  | 31 | 5 |  | 0 | 0 |
|  | 15 | 0 |  | 0 | 0 |
| 19 | 500 | 5 | 1 | 5 | 4 |
|  | 250 | 5 |  | 5 | 4 |
|  | 125 | 5 |  | 5 | 3 |
|  | 62 | 5 |  | 5 | 1 |
|  | 31 | 5 |  | 4 | 0 |
|  | 15 | 5 |  | 3 | 0 |
| 20 | 500 | 5 | 1 | 4 | 5 |
|  | 250 | 5 |  | 5 | 3 |
|  | 125 | 5 |  | 4 | 3 |
|  | 62 | 5 |  | 1 | 0 |
|  | 31 | 5 |  | 1 | 0 |
|  | 15 | 5 |  | 0 | 0 |
| 21 | 500 | 5 | 0 | 0 | 3 |
|  | 250 | 5 |  |  | 4 |
|  | 125 | 4 |  |  | 4 |
|  | 62 | 1 |  |  | 4 |
|  | 31 | 0 |  |  | 3 |
|  | 15 | 0 |  |  | 1 |

Because of the high degree of efficacy of the compounds disclosed herein, particularly those which are useful principally as miticides, it is preferred to apply the compounds to the foliage of infested plants in combination with a major proportion of an inert diluent. Water or a cheap powdered solid are conventionally used as diluents and are preferred. The minimum effective amount varies from species to species and to some extent from compound to compound, as shown in the data tabulated above. In general, any concentration of miticidal compounds greater than 15 ppm will accomplish a degree of control of mites. Higher concentrations may be advisable for more lasting control, depending to some extent on anticipated weather conditions and other factors. In some applications it is desirable to use a compound which has a clearly defined threshhold concentration, below which remaining traces of the compound will not be toxic. This characteristic may be observed in the test results on a few compounds in the foregoing table.

In combating insects and mites it is not necessary and it may even be undesirable to produce 100 percent kills in some situations. It may be preferable to kill only a majority of the pests, so as to avoid the development of resistant strains and prevent competing species from gaining an advantage. For these applications, compounds may be selected by using the data tabulated above as a guide. It will be understood that the term "combating" as used herein refers to killing and preventing propagation of a substantial proportion of the insect and mite population, sufficient to keep these pests under control.

I claim:
1. 3-Fluorosulfonyl-5-tert.butyl-4H-1,2,4-triazole.
2. 3-Fluorosulfonyl-5-methyl-4H-1,2,4-triazole.
3. 3-Fluorosulfonyl-5-propyl-4H-1,2,4-triazole.
4. 3-Fluorosulfonyl-5-isopropyl-4H-1,2,4-triazole.
5. 3-Fluorosulfonyl-5-cyclopropyl-4H-1,2,4-triazole.
6. 3-Fluorosulfonyl-5-butyl-4H-1,2,4-triazole.
7. 3-Fluorosulfonyl-5-(2-methylpropyl)-4H-1,2,4-triazole.
8. 3-Fluorosulfonyl-5-pentyl-4H-1,2,4-triazole.
9. 3-Fluorosulfonyl-5-(1-ethylpropyl)-4H-1,2,4-triazole.
10. A method of combating insects and mites which comprises applying to the foliage of plants infested with insects and mites an effective amount of a compound having the structural formula

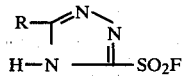

including tautomeric forms thereof, in which R is hydrogen, $C_1$ to $C_6$ alkyl, branched or unbranched, benzyl, phenyl or $C_3$ to $C_6$ cycloalkyl, in combination with a major proportion of an inert diluent.

11. A method of combating insects and mites which comprises applying to the foliage of plants infested with insects and mites an effective amount of 3-fluorosulfonyl-5-tert.butyl-4H-1,2,4-triazole.

12. A method of combating insects and mites which comprises applying to the foliage of plants infested with insects and mites an effective amount of 3-fluorosulfonyl-4H-1,2,4-triazole.

13. A method of combating insects and mites which comprises applying to the foliage of plants infested with insects and mites an effective amount of 3-fluorosulfonyl-5methyl-4H-1,2,4-triazole.

14. A method of combating insects and mites which comprises applying to the foliage of plants infested with insects and mites an effective amount of 3-fluorosulfonyl-5-ethyl-4H-1,2,4-triazole.

15. A method of combating insects and mites which comprises applying to the foliage of plants infested with insects and mites an effective amount of 3-fluorosulfonyl-5-propyl-4H-1,2,4-triazole.

16. A method of combating insects and mites which comprises applying to the foliage of plants infested with insects and mites an effective amount of 3-fluorosulfonyl-5-isopropyl-4H-1,2,4-triazole.

17. A method of combating insects and mites which comprises applying to the foliage of plants infested with insects and mites an effective amount of 3-fluorosulfonyl-5-cyclopropyl-4H-1,2,4-triazole.

18. A method of combating insects and mites which comprises applying to the foliage of plants infested with insects and mites an effective amount of 3-fluorosulfonyl-5-butyl-4H-1,2,4-triazole.

19. A method of combating insects and mites which comprises applying to the foliage of plants infested with insects and mites an effective amount of 3-fluorosulfonyl-5-benzyl-4H-1,2,4-triazole.

20. A method of combating insects and mites which comprises applying to the foliage of plants infested with insects and mites an effective amount of 3-fluorosulfonyl-5-(2-methylpropyl)-4H-1,2,4-triazole.

21. A method of combating insects and mites which comprises applying to the foliage of plants infested with insects and mites an effective amount of 3-fluorosulfonyl-5-pentyl-4H-1,2,4-triazole.

22. A method of combating insects and mites which comprises applying to the foliage of plants infested with insects and mites an effective amount of 3-fluorosulfonyl-5-(1ethylpropyl)-4H-1,2,4-triazole.

23. 3-Fluorosulfonyl-5-methoxymethyl-4H-1,2,4-triazole.

24. 3-Fluorosulfonyl-5-(1-phenoxyethyl)-4H-1,2,4-triazole.

25. 3-Fluorosulfonyl-5-(1-heptyl)-4H-1,2,4-triazole.

26. 3-Fluorosulfonyl-5-(3-methylbutyl)-4H-1,2,4-triazole.

27. 3-Fluorosulfonyl-5-(2,2-dimethylpropyl)-4H-1,2,4-triazole.

28. 3-Fluorosulfonyl-5-(2-pentyl)-4H-1,2,4-triazole.

29. 3-Fluorosulfonyl-5-(3-heptyl)-4H-1,2,4-triazole.

30. A method of combating insects and mites which comprises applying to the foliage of plants infested with insects and mites an effective amount of 3-fluorosulfonyl-5-methoxymethyl-4H-1,2,4-triazole.

31. A method of combating insects and mites which comprises applying to the foliage of plants infested with insects and mites an effective amount of 3-fluorosulfonyl-5-(1-phenoxyethyl)-4H-1,2,4-triazole.

32. A method of combating insects and mites which comprises applying to the foliage of plants infested with insects and mites an effective amount of 3-fluorosulfonyl-5-phenyl-4H-1,2,4-triazole.

33. A method of combating insects and mites which comprises applying to the foliage of plants infested with insects and mites an effective amount of 3-fluorosulfonyl-5-(1-heptyl)-4H-1,2,4-triazole.

34. A method of combating insects and mites which comprises applying to the foliage of plants infested with insects and mites an effective amount of 3-fluorosulfonyl-5-(3-methylbutyl)-4H-1,2,4-triazole.

35. A method of combating insects and mites which comprises applying to the foliage of plants infested with insects and mites an effective amount of 3-fluorosulfonyl-5-(2,2-dimethylpropyl)-4H-1,2,4-triazole.

36. A method of combating insects and mites which comprises applying to the foliage of plants infested with insects and mites an effective amount of 3-fluorosulfonyl-5-(2-pentyl)-4H-1,2,4-triazole.

37. A method of combating insects and mites which comprises applying to the foliage of plants infested with insects and mites an effective amount of 3-fluorosulfonyl-5-(3-heptyl)-4H-1,2,4-triazole.

38. A method of combating insects and mites which comprises applying to the foliage of plants infested with insects and mites an effective amount of 3-fluorosulfonyl-5-cyclohexyl-4H-1,2,4-triazole.

* * * * *